United States Patent
Buza (10) Patent No.: US 10,595,758 B2
(45) Date of Patent: Mar. 24, 2020

(54) METHOD AND APPARATUS FOR DETERMINING ONSET OF HYPOXIA

(71) Applicant: Southern Aeromedical Institute, Inc., Melbourne, FL (US)

(72) Inventor: Paul Buza, Grant, FL (US)

(73) Assignee: Southern Aeromedical Institute, Inc., Melbourne, FL (US)

( * ) Notice: Subject to any disclaimer, the term of this patent is extended or adjusted under 35 U.S.C. 154(b) by 252 days.

(21) Appl. No.: 15/432,253

(22) Filed: Feb. 14, 2017

(65) Prior Publication Data

US 2017/0325727 A1    Nov. 16, 2017

Related U.S. Application Data

(60) Provisional application No. 62/335,175, filed on May 12, 2016.

(51) Int. Cl.
*A61B 5/1455*     (2006.01)
*A62B 18/02*      (2006.01)
(Continued)

(52) U.S. Cl.
CPC ........ *A61B 5/14551* (2013.01); *A61B 5/0022* (2013.01); *A61B 5/02416* (2013.01);
(Continued)

(58) Field of Classification Search
CPC . A61B 5/0205; A61B 5/7275; A61B 5/14551; A61B 5/021; A61B 5/0836; A61B 5/087; A61B 5/412; A61B 5/4818; A61B 5/746; A61B 5/024; A61B 5/08; A61B 5/726; A61B 5/7267; A61B 5/02055; A61B 5/145; A61B 5/0816; A61B 5/742; A61B 5/082; A61B 5/4836; A61B 5/00; A61B 5/02405; A61B 5/02416; A61B 5/0476; A61B 5/14542; A61B 5/4094; A61B 5/02438; A61B 5/0452; A61B 5/7246;
(Continued)

(56) References Cited

U.S. PATENT DOCUMENTS

4,198,213 A    4/1980  Mannatt
4,651,728 A    3/1987  Gupta
(Continued)

*Primary Examiner* — Sean P Dougherty
*Assistant Examiner* — Benjamin S Melhus
(74) *Attorney, Agent, or Firm* — Beusse, Wolter, Sanks & Maire PLLC; John L DeAngelis (57) ABSTRACT

A method is presented for determining onset of hypoxia of an occupant in an aircraft. The method includes measuring a physiological parameter of the occupant and comparing a value based on the physiological parameter with a threshold value. The method also includes measuring a pressure within a cabin of the aircraft and comparing the pressure with a pressure threshold value. The method also includes determining onset of hypoxia of the occupant based on both of the comparing steps. The method also includes communicating an alert to the occupant using a device detectable by one or more senses of the occupant. An apparatus is also provided for determining onset of hypoxia. The apparatus includes a pressure sensor to measure the pressure, a pulse oximeter to measure the physiological parameter, an alert device to communicate the alert to the occupant and a processor to perform one or more steps of the method.

14 Claims, 6 Drawing Sheets

(51) Int. Cl.
*A62B 7/14* (2006.01)
*A61B 5/00* (2006.01)
*A61B 5/024* (2006.01)
*G16H 40/67* (2018.01)

(52) U.S. Cl.
CPC .......... *A61B 5/6803* (2013.01); *A61B 5/7246* (2013.01); *A61B 5/7282* (2013.01); *A61B 5/742* (2013.01); *A61B 5/7405* (2013.01); *A61B 5/746* (2013.01); *A61B 5/7455* (2013.01); *G16H 40/67* (2018.01); *A61B 2503/22* (2013.01); *A61B 2560/0242* (2013.01)

(58) Field of Classification Search
CPC ....... A61B 5/7264; A61B 5/01; A61B 5/0871; A61B 5/1118; A61B 5/7257; A61B 5/7282; A61B 5/743; A61B 5/002; A61B 5/0022; A61B 5/0488; A61B 5/091; A61B 5/11; A61B 5/1117; A61B 5/4848; A61B 5/686; A61B 5/026; A61B 5/04012; A61B 5/0402; A61B 5/042; A61B 5/14503; A61B 5/14532; A61B 5/14539; A61B 5/1455; A61B 5/14552; A61B 5/486; A61B 5/7235; A61B 5/0456; A61B 5/0833; A61B 5/4035; A61B 5/4839; A61B 5/4866; A61B 5/72; A61B 5/7203; A61B 5/7278; A61B 5/0059; A61B 5/0077; A61B 5/02; A61B 5/022; A61B 5/02433; A61B 5/02455; A61B 5/028; A61B 5/0295; A61B 5/0404; A61B 5/0484; A61B 5/0533; A61B 5/0826; A61B 5/097; A61B 5/1135; A61B 5/14546; A61B 5/162; A61B 5/411; A61B 5/415; A61B 5/418; A61B 5/6826; A61B 5/6852; A61B 5/0002; A61B 5/0006; A61B 5/0013; A61B 5/0031; A61B 5/0082; A61B 5/02007; A61B 5/02028; A61B 5/02116; A61B 5/02125; A61B 5/02141; A61B 5/0215; A61B 5/02427; A61B 5/04001; A61B 5/04017; A61B 5/04325; A61B 5/046; A61B 5/0464; A61B 5/0478; A61B 5/053; A61B 5/1107; A61B 5/1112; A61B 5/1113; A61B 5/1116; A61B 5/1121; A61B 5/113; A61B 5/1176; A61B 5/14553; A61B 5/222; A61B 5/4041; A61B 5/42; A61B 5/4227; A61B 5/441; A61B 5/445; A61B 5/447; A61B 5/4509; A61B 5/4812; A61B 5/4833; A61B 5/4869; A61B 5/4872; A61B 5/4884; A61B 5/6804; A61B 5/6814; A61B 5/6815; A61B 5/6824; A61B 5/6825; A61B 5/6843; A61B 5/6898; A61B 5/7207; A61B 5/7221; A61B 5/725; A61B 5/7285; A61B 5/74; A61B 5/7445; A61B 5/747; A61B 5/7475
See application file for complete search history.

(56) References Cited

U.S. PATENT DOCUMENTS

| | | | |
|---|---|---|---|
| 5,372,134 A * | 12/1994 | Richardson | A61B 5/02422 600/323 |
| 6,401,487 B1 | 6/2002 | Kolitar | |
| 6,923,183 B2 | 8/2005 | Martinez | |
| 7,082,946 B2 | 8/2006 | Farin | |
| 7,383,105 B2 * | 6/2008 | Conroy, Jr. | B64D 13/00 244/118.5 |
| 9,102,417 B1 * | 8/2015 | Young | A61B 5/18 |
| 9,919,712 B1 * | 3/2018 | Doyen | B60W 40/08 |
| 2004/0206353 A1 * | 10/2004 | Conroy, Jr. | A61B 5/14551 128/204.23 |
| 2017/0000339 A1 * | 1/2017 | Di Statsi | A61B 5/14542 |

* cited by examiner

METHOD AND APPARATUS FOR DETERMINING ONSET OF HYPOXIA

CROSS REFERENCE TO RELATED APPLICATIONS

This application is a Non-Provisional Patent Application that claims the benefit to U.S. Provisional Patent Application No. 62/335,175 filed on May 12, 2016, and incorporated by reference herein in its entirety.

FIELD

This invention relates to a method and training system for determining onset of hypoxia of an individual. More particularly, the invention relates to a method and apparatus for determining onset of hypoxia of a pilot flying a pressurized aircraft.

BACKGROUND

Prior art conventional training methods and systems rely only on subjective symptoms of hypoxia to determine the point at which the user must don his oxygen mask. Such symptoms may include: confusion, fast heart rate, rapid breathing, shortness of breath, tunnel vision, and tingling of the extremities. Measurable quantitative physiological symptoms have not been used.

These conventional training methods and systems have remained arbitrary and unchanged for over 50 years and do not utilize realistic flight scenarios nor rely on objective and/or true physiological parameters. Conventional training methods and systems do not utilize flight simulators or realistic ATC (air traffic controller) communications, nor do they use biomedical monitoring to determine endpoints (i.e., the time at which the user should don his mask).

In addition, these conventional training methods do not provide individualized training for recognizing or predicting the onset of hypoxia. Instead, the training is performed in large group settings, which are not consistent with the ergonomic or human factors model of cockpit training.

SUMMARY

In one embodiment of the present invention, a method is presented for determining onset of hypoxia of an occupant in an aircraft. The method includes measuring a physiological parameter of the occupant with a first sensor and comparing a value of a parameter based on the physiological parameter with a threshold value using a processor. The method also includes measuring a pressure within a cabin of the aircraft with a second sensor and comparing the pressure with a pressure threshold value using the processor. The method also includes determining onset of hypoxia of the occupant based on both of the comparing steps. The method also includes communicating an alert to the occupant using a device detectable by one or more senses of the occupant, where the communicating step is based on the determining step.

In another embodiment of the present invention, an apparatus is provided for determining onset of hypoxia of the occupant in the aircraft. The apparatus includes a pressure sensor configured to measure a pressure within a cabin of the aircraft and an alert device configured to be detected by one or more senses of the occupant. The apparatus also includes a pulse oximeter configured to measure an oxygen saturation level and a heart rate of the occupant. The apparatus also includes a processor configured to perform one or more steps of the method above.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus is described to determine onset of hypoxia. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

While the conventional methods and systems may be adequate for basic hypoxia training the inventor has recognized that they fail to accurately recreate the scenario environment in which an emergency would occur. Additionally, the inventor recognized that despite the provision of such conventional training methods to the aviation industry at large, significant fatalities continue to occur worldwide.

Since 1999 numerous decompression events and over 140 fatalities have occurred due primarily to the lack of understanding of the unique characteristics of "slow onset hypoxia." In particular, no training methods are available for this condition. The inventor developed a training method and system that addresses these identified drawbacks of conventional methods and systems for determining onset of hypoxia.

In some embodiments, hypoxia symptoms begin to present when the oxygen saturation level falls to an oxygen saturation level threshold (e.g. about 92%). Additionally, as the oxygen saturation level declines the heart rate increases. However, the inventor recognized that basing the onset of a hypoxia event solely on the oxygen saturation level is problematic because it leads to false positive alarms, i.e., indicating hypoxia onset when the decline in oxygen saturation may be due to a component malfunction that causes an inaccurate oxygen saturation reading. False alarms should be avoided in the aircraft environment.

The inventor overcame the drawbacks of solely basing onset of hypoxia on oxygen saturation level, by developing a method and apparatus that integrates measurable physiological parameters along with accurate flight deck instrumentation simulation to improve the quality of training to prevent such hypoxia events. In some embodiments, the present invention is directed toward simulating such an event, measuring and analyzing relevant physiological parameters, and examining the symptoms that occur prior to and during such an event.

In some embodiments, the invention relates to pilots who fly pressurized aircraft to teach them the dangers of hypoxia in the event of cabin depressurization, which otherwise would result in loss of consciousness or incapacitation. In other embodiments, when undergoing training according to the invention, the apparatuses and methods employed measure physiological conditions that would occur in a real-world aircraft environment during a hypoxia event. In an example embodiment, the invention relates real-time physiological monitoring to the emergency response protocols needed to avoid a potential catastrophe. In another example embodiment, the training provided according to the invention should be taken by all crew members, especially those who are expected to respond to emergency situations aboard the aircraft.

In some embodiments, the methods and the systems of the invention are centered around the innovative concept of utilizing multiple physiological data garnered by micro-sensors embedded within the user's (e.g., pilot's) headset that can alert the pilot to a dangerous cabin depressurization based on objective and reliable physiological data, even before he is subjectively aware of the depressurization. Conventional prior art training methods do not utilize such data and instead rely on the pilot's ability to feel the sensations of low oxygen, which is less reliable and often subject to wide variations between each person.

In some embodiments, the methods and systems of the invention determine blood oxygen levels and heart rate responses even before the pilot is aware of such and will alert him or her to don the oxygen mask and begin emergency response procedures. In these embodiments, this data is reliable based upon original research performed by the inventor to ensure its statistical reliability and eliminate unacceptable false alarms.

In some embodiments, the apparatuses and methods of the present invention utilize micro-sensors contained within a headset worn by the cockpit crew, with the data collection and analysis controlled by a computer or processor (e.g., a microchip) also in the headset and executing an original algorithm that triggers an auditory and haptic response to alert the pilot to the need for donning the oxygen mask.

Hypoxia is a condition in which the body or a region of the body is deprived of adequate oxygen supply at the tissue level. Hypoxia may be classified as either generalized, affecting the whole body, or local, affecting a region of the body. Although hypoxia is often a pathological condition, variations in arterial oxygen concentrations can be part of the normal physiology, for example, during hypoventilation training or strenuous physical exercise. Generalized hypoxia occurs in healthy people when they ascend to high altitude, where it causes altitude sickness leading to potentially fatal complications: high altitude pulmonary edema (HAPE) and high altitude cerebral edema (HACE). A mild and non-damaging intermittent hypoxia is used intentionally during altitude trainings to develop an athletic performance adaptation at both the systemic and cellular level.

The symptoms of generalized hypoxia depend on its severity and acceleration of onset. In the case of altitude sickness, where hypoxia develops gradually, the symptoms include lightheadedness/fatigue, numbness/tingling of extremities, nausea, and anoxia. In severe hypoxia, or hypoxia of very rapid onset, ataxia, confusion/disorientation/hallucinations/behavioral change, severe headaches/reduced level of consciousness, papilloedema, breathlessness, pallor, tachycardia, and pulmonary hypertension eventually leading to the late signs cyanosis, slow heart rate/cor pulmonale, and low blood pressure followed by death. Because hemoglobin is a darker red when it is not bound to oxygen (deoxyhemoglobin), as opposed to the rich red color that it has when bound to oxygen (oxyhemoglobin), when seen through the skin it has an increased tendency to reflect blue light back to the eye. In cases where the oxygen is displaced by another molecule, such as carbon monoxide, the skin may appear 'cherry red' instead of cyanotic.

Pulse oximetry is a noninvasive method for monitoring a pilot's oxygen saturation ($SO_2$). Its reading of SpO2 (peripheral oxygen saturation) is not always identical to the reading of $SaO_2$ (arterial oxygen saturation) from arterial blood gas analysis, but the two are correlated well enough that the safe, convenient, noninvasive, inexpensive pulse oximetry method is valuable for measuring oxygen saturation in clinical use. In one embodiment, a transmissive application mode, a sensor device is placed on a thin part of the pilot's body, usually a fingertip or earlobe, or across a foot. The device passes two wavelengths of light through the body part to a photodetector. It measures the changing absorbance at each of the wavelengths, allowing it to determine the absorbances due to the pulsing arterial blood alone, excluding venous blood, skin, bone, muscle, fat, and (in most cases) nail polish.

In another embodiment, reflectance pulse oximetry may be used as an alternative to transmissive pulse oximetery described above. This method does not require a thin section of the pilot's body and is therefore well suited to a universal application such as the feet, forehead, neck, face and chest.

Figure 1A:
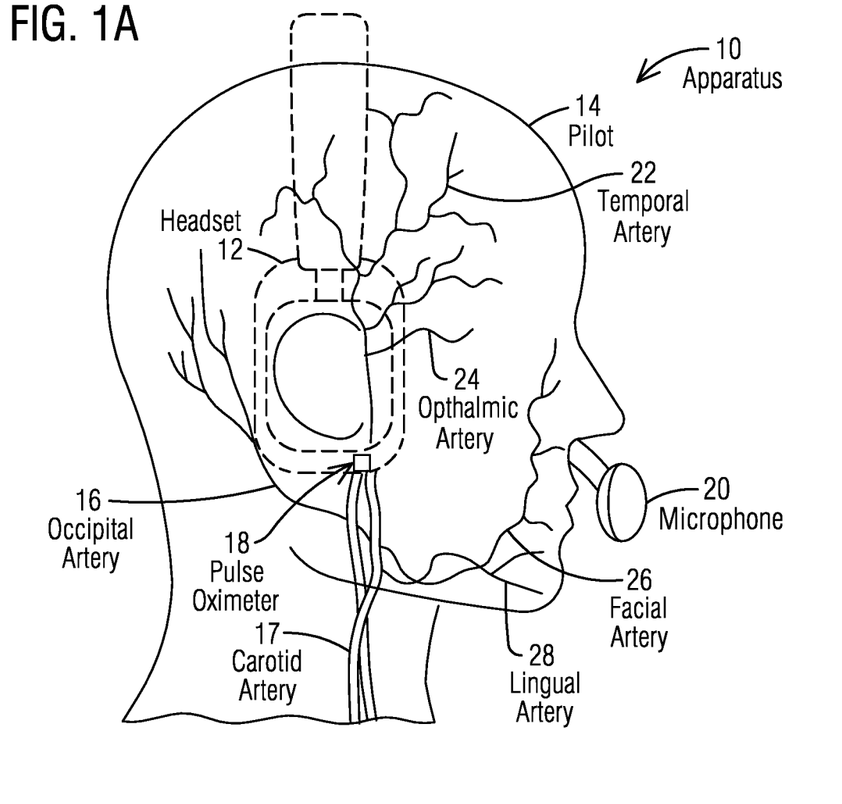
FIG. 1A is a side cut away view that illustrates an example of an apparatus for determining onset of hypoxia of the pilot in the aircraft, according to one embodiment.
Figure 1B:
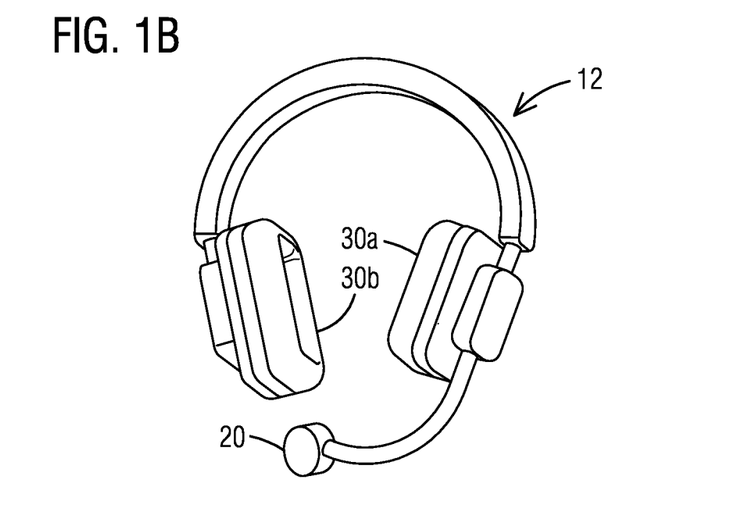
FIG. 1B is a perspective view that illustrates an example of a headset of the apparatus of FIG. 1A, according to one embodiment.

FIG. 1A is a side cut away view that illustrates an example of an apparatus 10 for determining onset of hypoxia of an occupant (e.g. the pilot 14) in the aircraft, according to one embodiment. FIG. 1B is a perspective view that illustrates an example of a headset 12 of the apparatus 10 of FIG. 1A, according to one embodiment. The headset 12 includes a pair of earpieces 30a, 30b and a microphone 20. Neither the pilot 14 nor the aircraft is part of the apparatus 10. In some embodiments, FIG. 1A illustrates the headset 12 and its position as worn by the occupant (e.g. pilot 14). In one embodiment, the headset 12 is a specialized adaptation of standard headset models that are worn by the pilot 14 in traditional fashion so as not to be unnecessarily cumbersome for the wearer. The use of an augmented conventional headset advantageously avoids potential distraction to flight responsibilities. In an example embodiment, the headset 12 is a Bose® A20 headset, made by the Bose® Corporation, Framingham, Mass.

As illustrated in FIG. 1A, when the headset 12 is worn in the conventional manner, an optical sensor (e.g. pulse oximeter 18) is disposed below the earpiece 30a, 30b on one or both sides of the head, proximate the occipital artery 16. In some embodiments, the optical sensor (e.g. pulse oximeter 18) is a pulse oximeter that uses infrared spectral shifting concepts (like conventional oximeters) to measure the oxygen content of the blood and heart rate of the pilot 14. In an example embodiment, the pulse oximeter 18 is a Nonin® 8000Q2 Purelight Oximeter, manufactured by Nonin Medical Inc., Plymouth Minn. In these embodiments, the pulse oximeter 18 is a reflectant pulse oximeter. In some embodiments, the pulse oximeter 18 is mounted to one or both earpieces 30a, 30b. In other embodiments, the pulse oximeter 18 is mounted adjacent to a base of one or both earpieces 30a, 30b. In still other embodiments, the pulse oximeter 18 is mounted to an inner surface of one or both earpieces 30a, 30b that is in contact with the pilot 14. In an example embodiment, the occipital artery 16 is chosen because it is a reliable indicator of the blood oxygen saturation level and the pulse oximeter 18 can be mounted to the headset 12 at the appropriate location and will not be cumbersome or distracting to the pilot. However, in other embodiments, the pulse oximeter 18 can be mounted at other locations along the headset 12 and positioned proximate to one of the carotid artery 17, the lingual artery 28, the facial artery 26, the ophthalmic artery 24 and the temporal artery 22. In still other embodiments, the pulse oximeter 18 need not be positioned on the headset 12. In one example embodiment, the pulse oximeter 18 is a transmissive pulse oximeter mounted to an ear lobe or a finger of the pilot 14.

In other embodiments, the pulse oximeter 18 is worn by occupants of the aircraft other than the pilot 14, such as flight crew and oxygen saturation level and heart rate data of the flight crew is measured and processed in the same manner as the data of the pilot 14 discussed herein. In some embodiments, the pulse oximeter 18 is worn by flight crew other than the pilot 14 for purposes of training the flight crew of determining onset of hypoxia. In an example embodiment, both the pilot 14 and co-pilot wear the headset 12 with the pulse oximeter 18.

Figure 2:
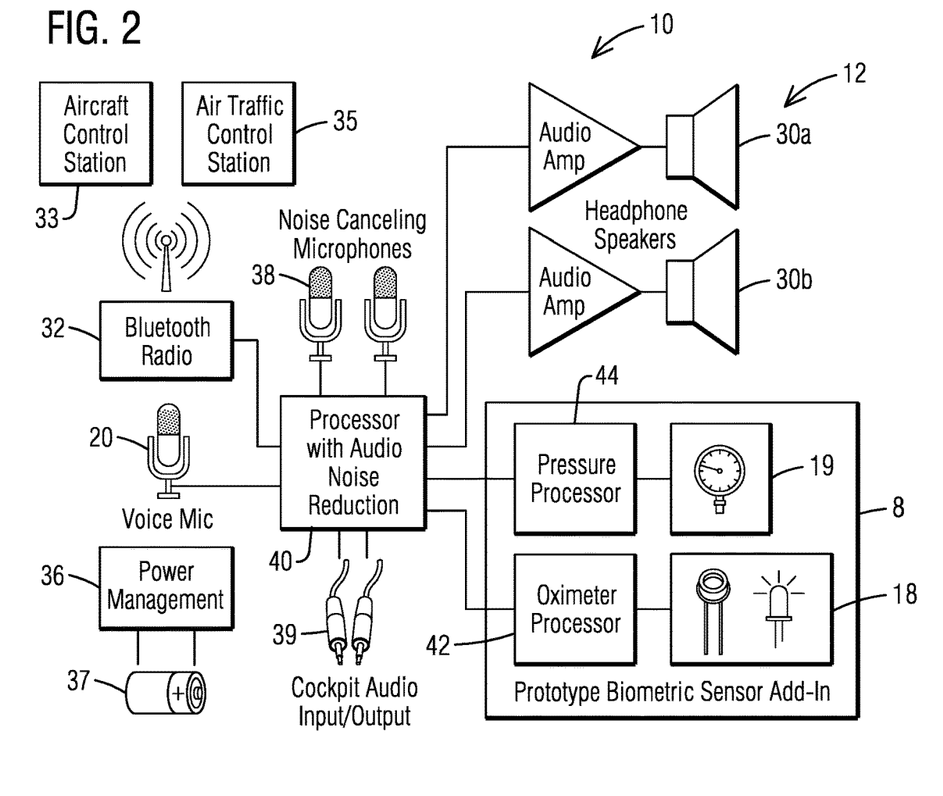
FIG. 2 is a block diagram that illustrates an example of the apparatus of FIG. 1A, according to one embodiment.

FIG. 2 is a block diagram that illustrates an example of the apparatus of FIG. 1A, according to one embodiment. In some embodiments, the block diagram of FIG. 2 depicts the hardware and software components within the headset 12 that measure and analyze the pilot's blood oxygen saturation and heart rate by utilizing micro-sensors embedded in the headset 12 as described in conjunction with FIG. 1. The anatomical location of the headset 12 lends itself well to obtain such data in a reliable but non intrusive fashion.

The headset 12 includes the earpieces 30a, 30b and the microphone 20 previously discussed with regard to FIG. 1. Additionally, as depicted in FIG. 2, the headset 12 includes coaxial audio input/output cables 39, noise cancelling microphones 38, power management 36 (connected to battery 37), and a processor 40 for processing audio noise reduction and a communication component 32 (e.g., Bluetooth radio) to relay collected and processed data to a control station 33 on the aircraft and/or to a control station 35 of air traffic control.

FIG. 2 also depicts a kit or add-on 8 that is used to supplement the headset 12 and form the apparatus 10. In other embodiments, the add-on 8 is an integral part of the headset 12. In some embodiments, as depicted in FIG. 2, the add-on 8 includes the pulse oximeter 18 that measures the oxygen saturation level and heart rate and an oximeter processor 42 that is used to compare one or more of the measured oxygen saturation level and heart rate with a threshold value. In other embodiments, the oximeter processor 42 is omitted and this function is performed by the headset processor 40, such that a software module is uploaded to the processor 40 for purposes of performing this comparison. In other embodiments, as depicted in FIG. 2, the add-on 8 includes a pressure sensor 19 that continuously measures pressure within a cabin of the aircraft. In some embodiments, the pressure sensor 19 is positioned in the cockpit of the aircraft to measure the pressure within the cockpit. In other embodiments, the pressure sensor 19 is positioned in one or more locations along an interior cabin of the aircraft. In some embodiments, the altimeter or pressure sensor 19 is located under a floor of the flight deck. In one embodiment, the pressure sensor 19 is in wireless communication with the headset processor 40. In another embodiment, the pressure sensor 19 is in wired communication with the headset processor 40. In some embodiments, this independent altimeter value in the algorithm ensures reliability that the cabin is decompressing. In an example embodiment, if the altimeter remains constant but the oxygen saturation level drops at a rate that exceeds a predetermined slope rate then the oxygen saturation decline is not due to cabin decompression, but indicates a possible medical condition of the pilot.

As depicted in FIG. 2, in some embodiments, the add-on 8 includes a pressure processor 44 that is used to compare the measured pressure from the sensor 19 with a pressure threshold. In some embodiments, the pressure processor 44 determines if the measured pressure is less than the pressure threshold. In one embodiment, the pressure threshold is in a range between 523 mm Hg (10,000 feet altitude) and 474 mm Hg (12,500 feet altitude). In other embodiments, the pressure threshold is in a range between 543 mm Hg (9,000 feet altitude) and 465 mm Hg (13,000 feet altitude). In other embodiments, the pressure processor 44 is omitted and this function is performed by the headset processor 40, such that a software module is uploaded to the processor 40 for purposes of performing this comparison.

As discussed below, the processed data from the pulse oximeter 18 and pressure sensor 19 will be used to determine an onset of hypoxia of the pilot and consider whether to trigger an alert to the pilot. In some embodiments, the alert is an auditory and/or a haptic alarm. In other embodiments, the processed data is used to consider whether to trigger an alert to the pilot and the flight crew and/or air traffic control.

Figure 3:
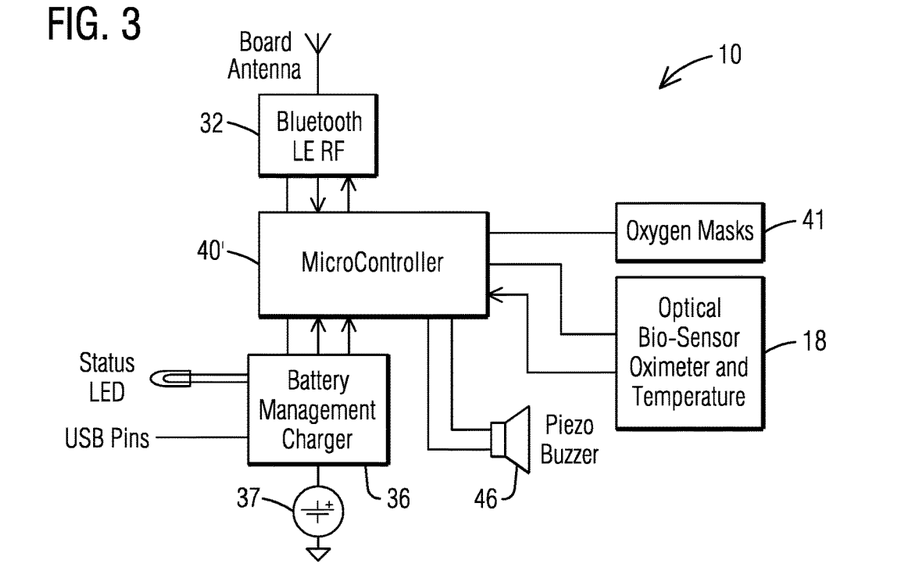
FIG. 3 is a block diagram that illustrates an example of the apparatus of FIG. 1A, according to one embodiment.

FIG. 3 is a block diagram that illustrates an example of the apparatus 10 of FIG. 1A, according to one embodiment. In some embodiments, the components of the apparatus 10 of FIG. 2 are employed to implement the present invention. In other embodiments, the components of the apparatus 10 of FIG. 3, are employed to implement the present invention. Like the processor 40 of FIG. 2, the microcontroller 40' of FIG. 3 requires original software programming to process the collected information. In some embodiments, the collected information includes measured oxygen saturation level from the pulse oximeter 18. In other embodiments, the collected information includes measured pressure from the pressure sensor 19. After processing, the data or alarms responsive thereto can be transmitted from the communication component 32 (e.g. Bluetooth) wirelessly to one or more of the control station 33 on the aircraft and the control station 35 of air traffic control.

As depicted in FIG. 3, in some embodiments, the apparatus 10 includes a device 46 such as a piezoelectric buzzer that is worn by the pilot 14 and alerts him or her to an impending hypoxia event by providing a haptic warning on the skin of the pilot. In other embodiments, the device 46 is an audio buzzer device that outputs an auditory warning that is detectable by the pilot 14. In still other embodiments, the device 46 is any device detectable by one or more senses of the pilot so to communicate an alert to the pilot 14 of an impending hypoxia event. In still other embodiments, the device 46 is located at one of the control station 33 on the aircraft or the control station 35 of air traffic control. In an example embodiment, the device 46 at one of the control station 33 or the control station 35 is a piezoelectric buzzer or audio buzzer to alert flight crew (at the control station 33) or an air traffic controller (at the control station 35) of the onset of hypoxia of the pilot 14. In an example embodiment, the remote device 46 located at one of the control station 33 or control station 35 receives a signal from the communication component 32.

Figure 4A:
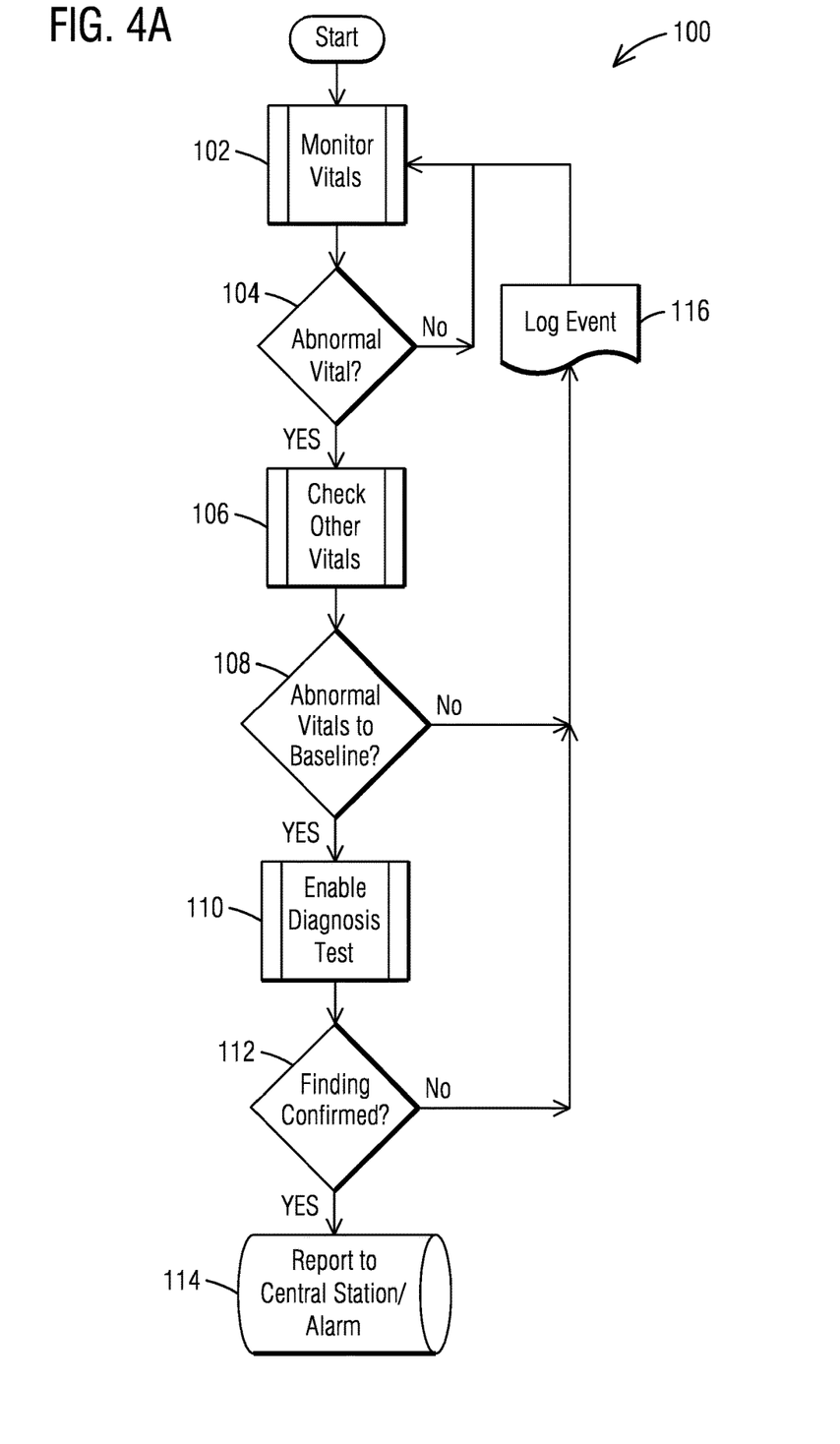
FIG. 4A is a block diagram that illustrates an example of a method for determining onset of hypoxia of the pilot in the aircraft, according to one embodiment.

FIG. 4A is a block diagram that illustrates an example of a method 100 for determining onset of hypoxia of the pilot 14 in the aircraft, according to one embodiment. In some embodiments, the flowchart of FIG. 4A is for the software program that executes within the processor 40 of FIG. 2 or the microcontroller 40' of FIG. 3. In some embodiments, the algorithm embedded within the software program triggers appropriate responses to and within the pilot and flight computers. At step 102, one or more vitals of the pilot 14 are monitored. In some embodiments, one or more physiological parameters of the pilot 14 are measured with a sensor. In one embodiment, in step 102, the oxygen saturation level and the heart rate of the pilot 14 are measured with the pulse oximeter 18. In some embodiments, the measured oxygen saturation level and heart rate are transmitted from the pulse oximeter 18 to the processor 40 of the headset 12. In other embodiments, the measured oxygen saturation level and heart rate are transmitted from the pulse oximeter 18 to the oximeter processor 42 of the add-on 8 to the headset 12.

In step 104, a determination is made whether the vitals monitored in step 102 are abnormal. In some embodiments, in step 104, the processor 40 of the headset 12 determines whether the measured oxygen saturation level from the pulse oximeter 18 is less than an oxygen saturation level threshold stored in a memory of the processor 40. In some embodiments, the oxygen saturation level threshold is defined as an oxygen level threshold at which the pilot 14 begins to experience symptoms of hypoxia. In other embodiments, the oxygen saturation level is defined as an oxygen level threshold at which the pilot 14 begins to experience one or more symptoms of hypoxia and below which the pilot 14 experiences increased symptoms of hypoxia. In an example embodiment, the stored oxygen saturation level threshold is about 63%. In another example embodiment, the stored oxygen saturation level threshold is about 73%. In another example embodiment, the stored oxygen saturation level threshold is in a range between about 63-92%. In some embodiments, symptoms of hypoxia begin at oxygen saturation levels less than about 92%. However, the inventor of the present invention observed that some subjects in a simulated pressure chamber (see FIGS. 6-7 below) did not experience hypoxia symptoms until the oxygen saturation levels fell to about 63%. Consequently, the oxygen saturation level threshold can be adjusted to any level in the range between 63-92%. If the processor 40 determines that the measured oxygen saturation level is less than the oxygen saturation level threshold, the method 100 proceeds to step 106. If the processor 40 determines that the measured oxygen saturation level is greater than the oxygen saturation level threshold, the method 100 proceeds back to step 102. In other embodiments, in step 102 the oxygen saturation level and heart rate of the pilot 14 are measured by the pulse oximeter 18. In step 104, the processor 40 determines whether the measured oxygen saturation level is less than the oxygen saturation level threshold and whether the measured heart rate is above a heart rate threshold stored in the memory of the processor 40.

Figure 5:
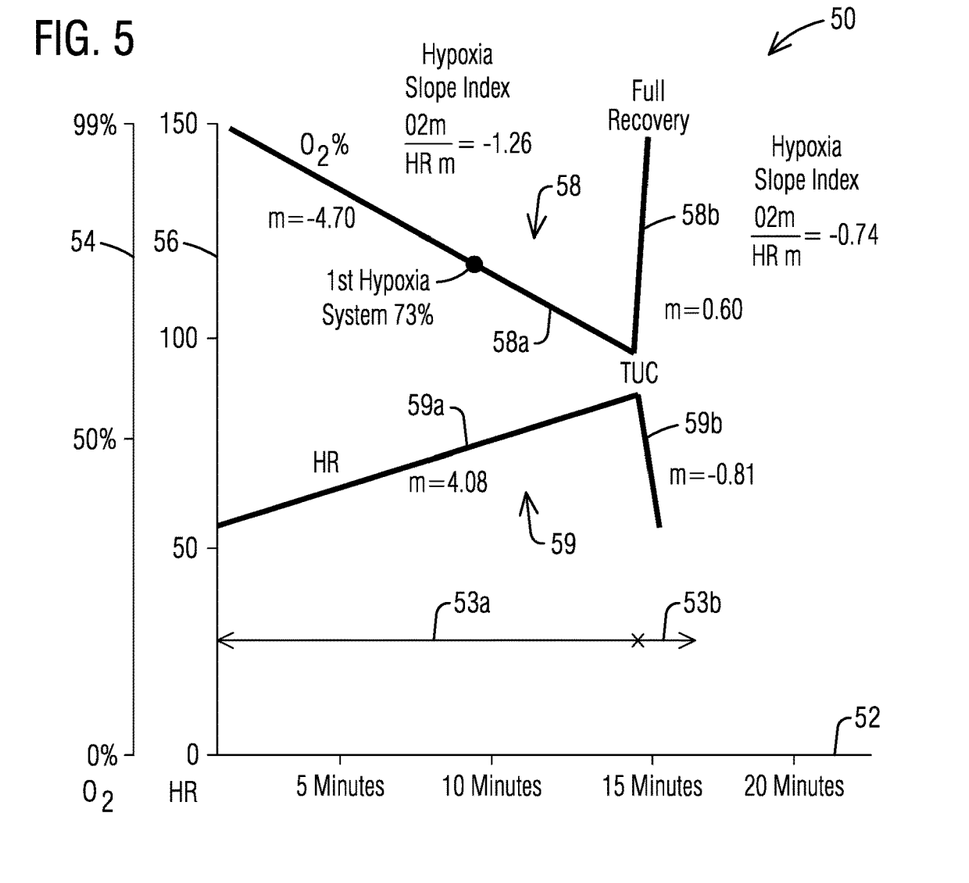
FIG. 5 is a graph that illustrates an example of an oxygen saturation level and heart rate of human subjects in a pressurized chamber over a time period, according to one embodiment.

In step 106, other vitals of the pilot 14 are checked. In some embodiments, in step 106, the oxygen saturation level and heart rate of the pilot 14 is measured by the pulse oximeter 18 over a time period. In some embodiments, the time period is the TUC or time period 53a discussed below. In other embodiments, the time period is a predefined time period, such as 5 minutes, for example. FIG. 5 is a graph 50 that illustrates an example of the oxygen saturation level 58 and heart rate 59 over a TUC (time of useful consciousness) or time period 53a, according to one embodiment. As discussed below, in some embodiments, the TUC or time period 53a is defined as a time period that ends when the pilot 14 experiences a threshold number of symptoms (e.g. three) of hypoxia. In other embodiments, the TUC or time period 53a is defined as a time period which ends when the oxygen saturation level 58 lowers to the oxygen saturation level threshold discussed above in step 104. In the example embodiment of FIG. 5, the TUC or time period 53a ends when the oxygen saturation level 58a lowers to an example oxygen saturation level threshold of about 63%. The horizontal axis 52 is time in units of minutes. The left vertical axis 54 is oxygen saturation level in units of percentage. The right vertical axis 56 is heart rate in units of beats per minute.

In step 108, a determination is made whether the vitals checked in step 106 are abnormal. In some embodiments, in step 108, the processor 40 calculates a first slope based on a rate of change of the oxygen saturation level 58a over the time period, such as the time period 53a. In these embodiments, in step 108, the processor 40 further calculates a second slope based on a rate of change of the heart rate 59a over the time period 53a. In these embodiments, in step 108, the processor 40 then calculates a slope index based on a ratio of the first slope to the second slope. In these embodiments, in step 108, the processor 40 then compares a magnitude of the slope index with a slope index range indicative of onset of hypoxia stored in the memory of the processor 40. In some embodiments, the slope index range is determined using a process involving a simulation chamber 70, as discussed further below. In an example embodiment, the processor 40 determines whether the magnitude of the slope index is within the slope index range. In one example embodiment, the slope index range is between about 0.9 and about 1.4. In another example embodiment, the slope index range is between about 1.0 and about 1.25. In yet another example embodiment, the slope index range is about 1.15. In step 108, if the processor 40 determines that the slope index is within the slope index range, the method proceeds to step 110. If the processor 40 determines that the slope index is not within the slope index range, the method proceeds to block 116. In block 116, an event is logged, such as an incident other than an onset of hypoxia. In one example embodiment, in block 116, it may be determined that the pulse oximeter 18 is malfunctioning and an alert may be generated to test or replace the pulse oximeter 18. In another example embodiment, in block 116, it may be determined that the pilot 14 is experiencing a medical condition other than hypoxia and an alert may be generated to perform a medical test of the pilot 14.

In step 110, a test is performed to confirm whether or not the pilot 14 is experiencing an onset of hypoxia. In some embodiments, in step 110, the pressure sensor 19 continuously measures the pressure within the cabin on the aircraft and continuously transmits this measured pressure to the processor 40 (or to the processor 44). In step 112, the processor 40 compares the measured pressure with the pressure threshold stored in a memory of the processor 40 that is associated with an onset of hypoxia in human subjects. In an example embodiment, in step 112, the processor 40 determines whether the measured pressure is less than the pressure threshold. If the processor 40 determines that the measured pressure is less than the pressure threshold, the method 100 moves to step 114.

In step 114, the processor 40 transmits a signal to the alert device 46 to alert the pilot 14 of the onset of hypoxia. Additionally, in some embodiments, the processor 40 transmits a signal to the communication component 32 to communicate a secondary alert to the control station 33 and/or control station 35. In an example embodiment, the secondary alert includes transmitting a signal to one or more displays at each of the control station 33 and control station 35 to output an image on the one or more displays, where the image includes text or symbols that convey the onset of hypoxia of the pilot 14.

In other embodiments, in step 114, the processor 40 transmits a signal to cause oxygen masks 41 to drop so that the pilot 14 (and other passengers) can wear the oxygen masks 41. In this embodiment, after the processor 40 causes the oxygen masks 41 to drop, steps 106 and 108 are repeated so to calculate the slope index over a recovery time period 53b (e.g. 60 seconds) after the pilot 14 wears the oxygen masks 41. In this embodiment, in step 108, the processor 40 compares the calculated slope index with a slope index range indicative of recovery from hypoxia. In an example embodiment, the slope index range indicative of recovery from hypoxia is in a range between about 0.6 and about 0.9. In another example embodiment, the slope index range indicative of recovery from hypoxia is about 0.74.

In some embodiments of the method 100, steps 110 and 112 are omitted in which case the method 100 moves from step 108 to block 114. In other embodiments of the method 100, steps 106 and 108 are performed prior to steps 102 and 104 (i.e. steps 102 and 104 are switched with steps 106 and 108). In still other embodiments of the method 100, steps 102 and 104 are omitted.

Figure 4B:
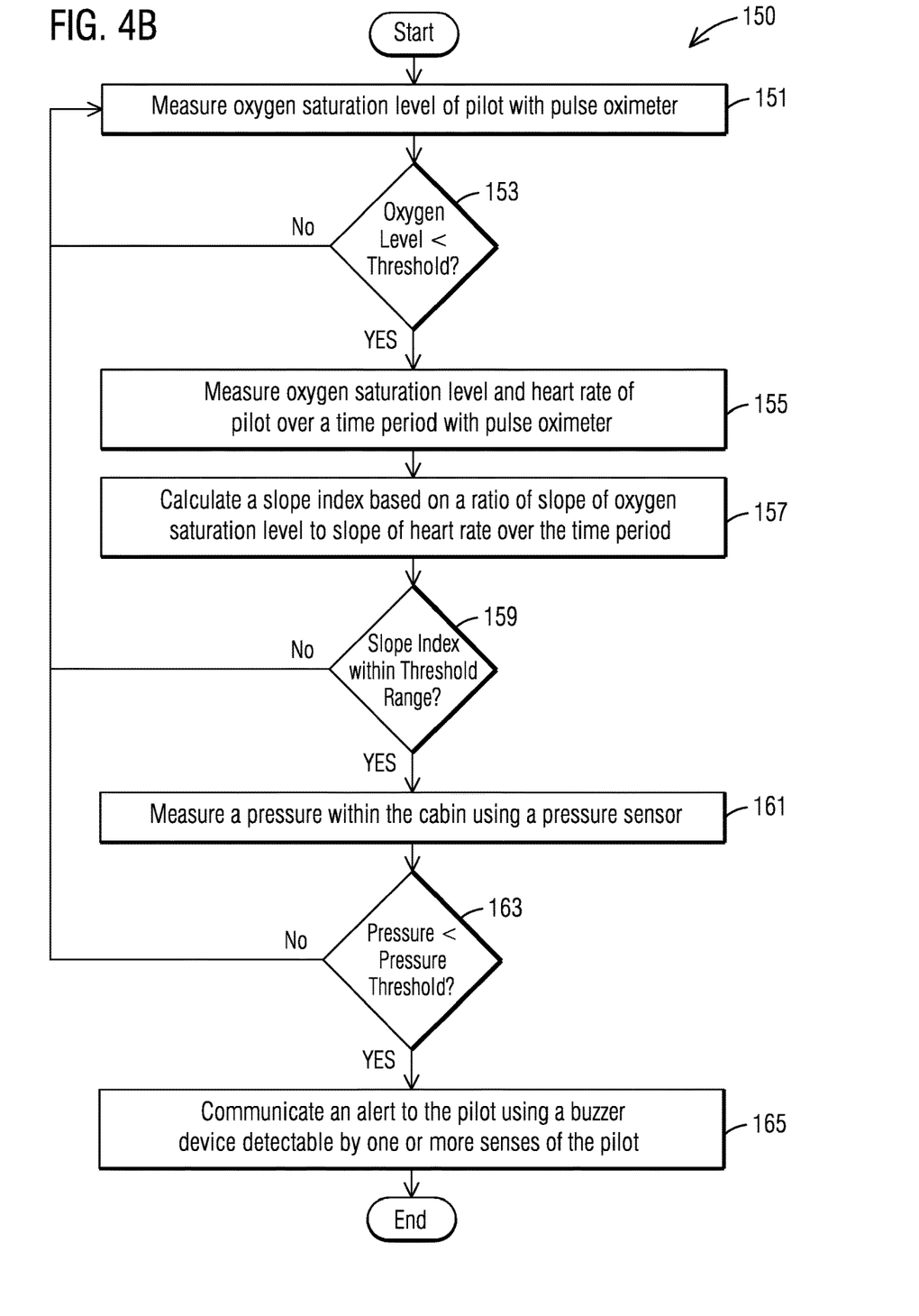
FIG. 4B is a block diagram that illustrates an example of a method for determining onset of hypoxia of the pilot in the aircraft, according to one embodiment.

FIG. 4B is a block diagram that illustrates an example of a method 150 for determining onset of hypoxia of the pilot 14 in the aircraft, according to one embodiment. The method 150 is similar to the steps discussed above with regard to the method 100. In step 151, a physiological parameter of the pilot 14 is measured with a sensor. In an example embodiment, in step 151, the oxygen saturation level of the pilot 14 is measured with the pulse oximeter 18.

In step 153, the processor 40 determines whether the measured oxygen saturation level is less than the oxygen saturation level threshold stored in the memory of the controller 40. If the determination in step 153 is positive, the method 150 proceeds to step 155. If the determination in step 153 is negative, the method 150 proceeds back to step 151.

In step 155, the oxygen saturation level 58 and heart rate 59 (see FIG. 5) of the pilot 14 is measured over a time period with the pulse oximeter 18. In one embodiment, the time period is the TUC or time period 53a. In other embodiments, the time period is a predefined time period, such as 5 minutes. In some embodiments, the TUC or time period 53a is about 15 minutes. In other embodiments, the time period 53a is in a range from 1-15 minutes.

In step 157, the slope index is calculated over the time period, such as the TUC or time period 53a. In step 159, the processor 40 determines whether the calculated slope index from step 157 is within the slope index range that is stored in the memory of the processor 40. If the calculated slope index is within the slope index range, the method 150 proceeds to step 161. If the calculated slope index is not within the slope index range, the method 150 proceeds back to step 151.

In step 161, the pressure within the aircraft cabin is measured with the pressure sensor 19. In step 163, the processor 40 determines whether the measured pressure within the aircraft cabin is less than the pressure threshold stored in the memory of the processor 40 indicating an onset of hypoxia. If the measured pressure is less than the pressure threshold, the method 150 moves to step 165. If the measured pressure is greater than the pressure threshold, the method 150 moves to step 151.

In step 165, the processor 40 communicates an alert to the pilot 14 using the buzzer device 46 detectable by one or more senses of the pilot 14. Additionally, in some embodiments, the processor 40 transmits a signal to the communication component 32 to communicate a secondary alert to one or more of the control station 33 and control station 35. In an example embodiment, the secondary alert includes transmitting a signal to one or more displays at each of the control station 33 and control station 35 to output an image on the one or more displays, where the image includes text or symbols that convey the onset of hypoxia of the pilot 14.

Table 1 below depicts the results of a detailed statistical analysis (as performed by the software program ANOVA) that supports the results of research of the inventor of the present invention into the physiological indicators of a hypoxia event. The statistical analysis was conducted on original data that relates the relationship of oxygen desaturation and changing heart rate in real time (i.e., slopes including a time parameter on the x-axis). It is described mathematically by the Slope Index (SI) that achieves statistical reliability as demonstrated by the ANOVA program analysis.

The Slope Index was developed by the inventor during real time research using a high altitude chamber to collect real time data from certified pilots and student pilots. The statistical analysis, as reflected in Table 1, of the slope index parameter is used so that oxygen saturation and heart beat measurements can reliably indicate a hypoxia event. In some embodiments, the slope index correlates the negative slope of the falling oxygen saturation level 58a with the positive slope of the increasing heart rate 59a. The inventor of the present invention recognized that this correlation is a useful mathematical finding that is statistically reliable in terms of predicting an onset of hypoxia.

TABLE 1

ANOVA[a]

| | Model | Sum of Squares | df | Mean Square | F | Sig. |
|---|---|---|---|---|---|---|
| 1 | Regression | 2156.601 | 3 | 718.867 | 4.522 | .007[b] |
| | Residual | 7311.879 | 46 | 158.964 | | |
| | Total | 9488.480 | 49 | | | |

| | | Unstandardized Coefficients | | Standardized Coefficients | | | 95.0% Confidence interval for B | |
|---|---|---|---|---|---|---|---|---|
| Model | | B | Std. Error | Beta | t | Sig. | Lower Bound | Upper Bound |
| 1 | (Constant) | 124.254 | 28.563 | | 4.876 | .000 | 70.765 | 177.724 |
| | Low O2 Sat | −.686 | .283 | −.340 | −2.421 | .019 | −1.256 | −.116 |
| | Low Heart Rt | .534 | .207 | .352 | 2.578 | .013 | .117 | .950 |
| | Time (min) | −.397 | .802 | −.073 | −.496 | .623 | −2.010 | 1.217 |

[a]Dependent Variable: highest heart rate
[b]Predictors: (Constant), time change (min), Lowest heart rate, Lowest O2
Dependent Variable: highest heart rate The columns of Table 1 include:
Sum of Squares: The total sum of squares helps express the total variation that can be attributed to various factors.
DF: Degrees of freedom
Mean Square: An estimate of the population variance based on the variability among a given set of measures.
F: The ratio of two mean square values.
Sig: Significance
T: Two way analysis of variance FIG. 5 illustrates the Slope Index concept. In some embodiments, the slope index is reliable as a predictor of the pilot's condition not only during decreasing oxygen levels but also during the recovery phase once an oxygen mask is donned.

FIG. 5 depicts that the oxygen saturation level 58 includes a decreasing level 58a during a time of useful consciousness (TUC) or time period 53a and an increasing level 58b during a recovery time period 53b, i.e. after the pilot 14 wears the oxygen mask 41. Similarly, FIG. 5 depicts that the heart rate 59 includes an increasing heart rate 59a during the TUC or time period 53a and a decreasing heart rate 59b during the recovery time period 53b, i.e. after the pilot wears the oxygen mask 41. In one embodiment, the TUC or time period 53a is defined as a time period over which the oxygen level 58a and heart rate 59a are measured and which ends after the pilot 14 experiences a threshold number of symptoms (e.g. three) of hypoxia. In other embodiments, the TUC or time period 53a ends after the pilot 14 experiences the threshold number of hypoxia symptoms along with recognizable neurocognitive impairment. In some embodiments, if the pilot 14 does not take certain action (e.g. don an oxygen mask) at the end of the TUC or time period 53a, a hypoxia event is likely to occur. In one example embodiment depicted in FIG. 5, the TUC or time period 53a continues beyond when the oxygen level 58a reaches about 73%, when a first hypoxia symptom is detected. However, in other embodiments, the TUC or time period 53a can end when the oxygen level 58a reaches about 73%. In another embodiment, the TUC or time period 53a is defined as a time period which ends when the oxygen level 58a reaches the oxygen saturation level threshold discussed in step 104. Although FIG. 5 depicts that the TUC or time period 53a is approximately 15 minutes and ends when the oxygen saturation level is at approximately 62%, this is merely one example of TUC or time period 53a. In other embodiments, the TUC or time period 53a ends when the oxygen saturation level 58a reaches the oxygen saturation level threshold stored in the processor 40 memory. In some embodiments, at the end of the TUC or time period 53a, the pilot 14 dons an oxygen mask, which commences the recovery time period 53b. The oxygen level 58b and heart rate 59b are then measured during the recovery time period 53b after the pilot 14 donned the oxygen mask. The recovery time period 53b is defined as the time period until the oxygen level 58b and heart rate 59b are back at safe levels (e.g. 99% for oxygen saturation level).

In one embodiment, the recovery time period 53b was measured, i.e. a period of time measured from when the pilot 14 dons the oxygen mask 41 until the oxygen saturation level 58 and heart rate 59 are at safe levels (e.g. 99% for oxygen saturation level). In an example embodiment, the average recovery time period 53b is approximately 60.13 seconds. In other example embodiments, the average recovery time period 53b is about 50-70 seconds. In some embodiments, if the oxygen saturation level 58 and heart rate 59 of the pilot 14 do not reach safe levels within about 50-70 seconds, the processor 40 is configured to transmit another alert to the buzzer 46 to alert the pilot 14 that the mask 41 may not be properly fitted or that the masks 41 may not be functioning correctly.

In some embodiments, the slope index (SI) graph 50 of FIG. 5 was developed to examine the real time mathematical relationship between oxygen saturation level 58a degradation and the compensatory heart rate 59a increase in a controlled ascent of an aircraft. In an example embodiment, the graph 50 was developed to examine the real time mathematical relationship between oxygen saturation level 58a degradation and compensatory heart rate 59a increase during a control ascent of about 1500 feet per minute. FIG. 5 depicts example slopes (using "m" for a numeric value of slope) for each of the oxygen saturation levels 58a, 58b and heart rate levels 59a, 59b. These example slopes are merely used to compute an example slope index of −1.15 during the TUC or time period 53a based on a first slope of −4.70 of the oxygen saturation level 58a and a second slope of 4.08 of the heart rate level 59a. Also, these example slopes are merely used to compute an example slope index of −0.74 during the recovery time period 53b based on a first slope of 0.60 of the oxygen saturation level 58b and second slope of −0.81 of the heart rate level 59b.

Figure 6:
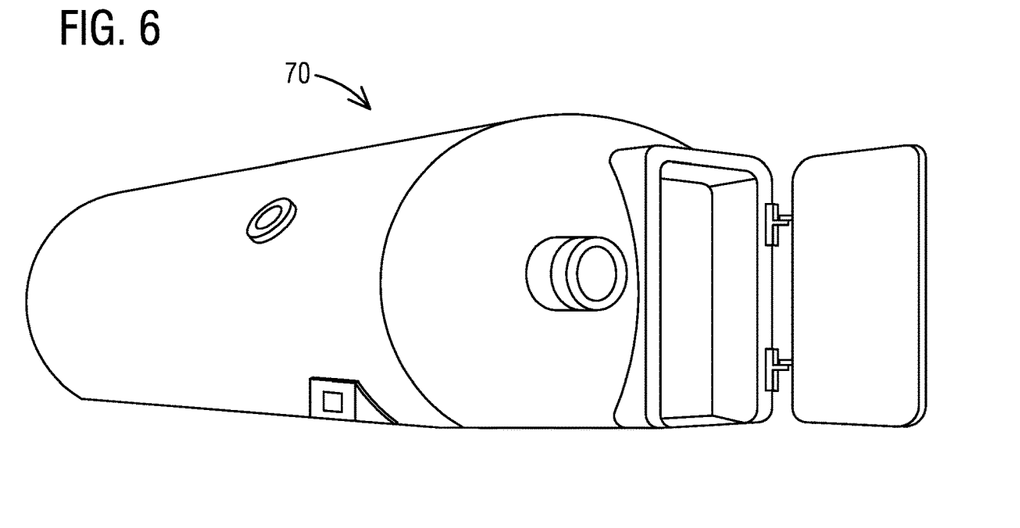
FIG. 6 is a perspective view that illustrates an example of the pressurized chamber used to generate the graph of FIG. 5, according to one embodiment.
Figure 7:
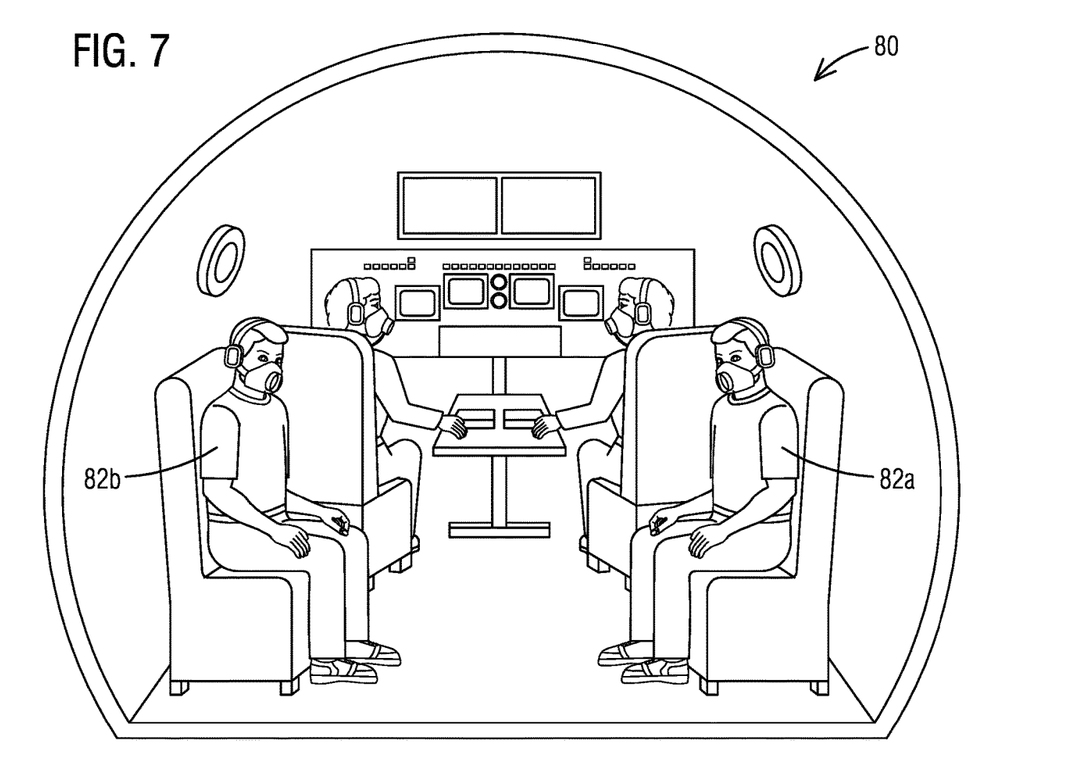
FIG. 7 is a view that illustrates an example of human subjects within an interior of the pressurized chamber of FIG. 6, according to one embodiment.

FIG. 6 is a perspective view that illustrates an example of a simulation pressurized chamber 70 used to generate the graph of FIG. 5, according to one embodiment. FIG. 7 is a view that illustrates an example of the human subjects 82a, 82b within an interior 80 of the pressurized chamber 70, according to one embodiment. In some embodiments, a pressure within the interior 80 of the pressurized chamber 70 is adjustable, to simulate a pressure change associated with a change in altitude of an aircraft. In some embodiments, a method is provided herein to measure the oxygen saturation level 58 and heart rate 59 of the plurality of human subjects 82a, 82b in the pressurized chamber 70 over the TUC or time period 53a and recovery time period 53b. In one embodiment, the apparatus 10 of FIG. 1A is worn by each human subject in the chamber 70 and the pulse oximeter 18 measures the oxygen saturation level and heart rate over the TUC or time period 53a and recovery time period 53b. In some embodiments, during the simulation, the oxygen saturation level and heart rate of each human subject is measured during the TUC or time period 53a which ends based on the threshold number (e.g. three) recognizable signs and symptoms of hypoxia along with recognizable neurocognitive impairment. At the end of TUC or time period 53a, the human subject dons an oxygen mask and the oxygen saturation level and heart rate are continuously measured during the recovery time period 53b (i.e. when oxygen saturation level 58b increases and heart rate 59b decreases).

A central processor (not shown) receives the measured oxygen saturation level and heart rate from each human subject in the chamber 70 and calculates the oxygen saturation level 58 and heart rate 59 based on a closest fit of the data from each human subject. In one embodiment, the oxygen saturation level 58 in the graph 50 is a least squares fit of the measured oxygen saturation levels of the plurality of human subjects over the time periods 53a, 53b. In another embodiment, the heart rate 59 in the graph 50 is a least squares fit of the measured heart rates of the plurality of human subjects over the time periods 53a, 53b. In an example embodiment, oxygen saturation level and heart rate of about 50 human subjects is measured over the time periods 53a, 53b, to calculate the oxygen saturation level 58 and heart rate 59. In an additional embodiment, the oxygen saturation level 58a and heart rate 59a is a least square fit of the measured oxygen saturation level and heart rate during the time period 53a or TUC. In another example embodiment, the oxygen saturation level 58b and heart rate 59b is a least square fit of the measured oxygen saturation level and heart rate during the recovery time period 53b (e.g. after each human subject donned the oxygen mask). In some embodiments, the central processor calculates the slope index associated with onset of hypoxia based on a ratio of the first slope of the oxygen saturation level 58a to the second slope of the heart rate 59a. In an example embodiment, the slope index is about −1.15 based on a ratio of the first slope of about −4.70 to the second slope of about 4.08. In other embodiments, the slope index is in a range between about −0.9 and about −1.4 or in a range between about −1.0 and about −1.25. In other embodiments, the central processor calculates the slope index associated with recovery from hypoxia during the recovery time period 53b based on a ratio of the slope of the first slope of the oxygen saturation level 58b to the second slop of the heart rate 59b. In an example embodiment as illustrated in FIG. 5, the slope index associated with recovery from hypoxia during the recovery time period 53b is about −0.74 based on a first slope associated with the O2 saturation level and a slope of about −0.60 and a second slope associated with the heart rate (HR) slope of about −0.81. In an example embodiment, the slope range is between about −0.6 and about −0.9. In some embodiments, a magnitude of the slope index associated with onset of hypoxia and a magnitude of the slope index associated with recovery from hypoxia are stored in the memory of the processor 40, for purposes of performing the method 100 of FIG. 4A or the method 150 of FIG. 4B.

In some embodiments, the pressure within the interior 80 of the pressurized chamber 70 is adjusted from a first pressure to a second pressure that is less than the first pressure over the TUC or time period 53a. In some embodiments, the first pressure is about 760 mm Hg (sea level) and the second pressure is about 349 mm Hg (20,000 feet). However, these values of the first and second pressure are merely examples and the embodiments of the invention are not limited to these particular first and second pressures. In some embodiments, the pressure is adjusted at an approximate fixed rate of change over time, such as a rate of change equivalent to an altitude increase of about 1500 feet per minute. In some embodiments, the pressure is adjusted for the TUC or time period 53a of about 15 minutes to simulate an altitude increase from about 5000 feet to about 23,000 feet. In an example embodiment, the rate of change of oxygen saturation (i.e., as a function of time) compared to the rate of change in heart rate (i.e., HR as a function of time) can be described mathematically as a constant. In an example embodiment, the constant does not change with rate of ascent. This concept is expressed mathematically as a ratio of these two values:

$$(\Delta O2/\Delta \text{ time}) = \text{slope of } O2 \text{ curve} \tag{1}$$

$$(\Delta HR/\Delta \text{ time}) = \text{slope of } HR \text{ curve} \tag{2}$$

$$\text{Slope of } O2/\text{slope of } HR = \text{slope index} = \text{constant} \tag{3}$$

In some embodiments, use of the slope index value increases the reliability of algorithmic decision-making to alert the crew of impending hypobaric hypoxia, and thereby preventing incapacitation.

In an example embodiment, data used to derive this relationship was taken from 50 healthy pilots ranging in age from 18 to 67. In another example embodiment, the simulated ascent in the chamber 70 began at 5000 feet of altitude ascending at a rate of 1500 feet per minute concluding at 23,000 feet where sufficient hypoxia was achieved. In an example embodiment, the average oxygen saturation of the human subjects at the end of the time period 53a or TUC was about 63%.

In some embodiments, a slope index or ratio value of 1.0 (ignoring the negative sign for convenience) would indicate a direct and one-to-one proportional relationship between the oxygen saturation level 58a and the heart rate 59a. The negative sign in the slope calculation merely indicates that the heart rate increases as the oxygen saturation decreases.

In some embodiments, values of the ratio that are about 1.0 (more accurately −1.0) are statistically reliable indicators of a hypoxia event. In one embodiment, values of the slope index from −1.0 to −1.25 (i.e. magnitude of about 1.0 to about 1.25) may be indicative of a hypoxia event and values less than −1.25 (for example −1.50) may be indicative of a component or equipment failure. In some embodiments, the actual results for a specific subject may vary from the expected −1.0 value due to personal variables that differ among subjects, such as anxiety levels, physical condition, smoking habits, etc.

In some embodiments, slope calculations during the recovery phase were calculated finding the first slope (i.e. slope O2) to be about −0.60 and the second slope (i.e. slope HR) to be about 0.81, resulting in a slope index of about −0.74. In an embodiment, this value or range of values can be used in algorithmic decision making to ensure crew recovery and test the quality of mask oxygenation.

In one embodiment, an average recovery time 53b to full recovery of oxygen saturation is about 60.13 seconds.

In an example embodiment, the slope index in both the hypoxia phase and the recovery phase appears to be directly proportional in relationship and is about −1.0 indicating an immediate and direct relationship between oxygen saturation and heart rate.

According to one embodiment, the algorithm employed in the method 100 or method 150 first measures the oxygen saturation and heart rate over a time interval 53a and calculates the slope index. If the result is within the slope index range (e.g. between about −1.0 and −1.25) then the algorithm measures the oxygen saturation level. If that value is less than an oxygen saturation level threshold (e.g. about 63%) an alarm is triggered. In this embodiment, steps 155, 157 and 159 are performed prior to steps 151, 153 of the method 150. Similarly, in this embodiment, steps 106 and 108 are performed prior to steps 102 and 104 of the method 100. In another embodiment, the oxygen saturation level threshold is about 75%.

In yet another embodiment of the method 100 or method 150, the oxygen saturation level is measured first and if that value is within a predetermined range or less than the oxygen saturation level threshold (e.g. about 63%) then the slope index is calculated from time-based oxygen saturation and heart rate values. If the slope index is within the slope index range (e.g. between about −1.0 and −1.25) then the alarm is triggered.

In some embodiments, the slope index can be calculated at periodic time intervals (e.g. every second) based on any number of current and past values of the oxygen saturation level and the heart rate.

In some embodiments, it is preferable to use both the saturation level and the heart rate values to avoid false alarms. Ideally the number of false alarms is zero. The inventor of the present invention recognized that, from a psychological perspective, too many (or any) false alarms may cause the pilot and flight crew to become complacent and simply ignore the alarms, at their peril. False alarms are also to be avoided because emergency conditions (e.g. a hypoxia event) aboard an aircraft cause major distractions for the flight crew—distractions that need to be minimized (or eliminated) by minimizing or eliminating all false alarms.

In some embodiments, during the recovery time period 53b a calculated slope index (e.g. a ratio of a change in oxygen saturation 58b and a change in heart rate 59b during the recovery phase) should reach a steady state value in a recovery time period (e.g. about one minute). If this does not occur then the oxygen mask may be faulty or not properly worn. In one embodiment the slope index during the recovery phase is also about one. In an example embodiment, another measure of a successful recovery phase is an oxygen saturation level 58b of about 99% after the recovery time period (e.g. one minute), which is the normal oxygen saturation level for a healthy individual at about sea level.

In some embodiments, a properly measured oxygen saturation value alone may be sufficient to alert the pilot to a hypoxia event and cause her to don an oxygen mask. In this embodiment, steps 155-163 of the method 150 are eliminated and a positive determination in step 153 leads to communicating the alert in step 165. In other embodiments, the measured oxygen saturation level being less than the oxygen saturation level threshold may indicate a component failure in the measuring apparatus (e.g. pulse oximeter 18). In some embodiments, the present invention objectively validates the oxygen saturation level by calculating the slope index and thereby provides an accurate assessment of the hypoxia event onset.

Figure 8:
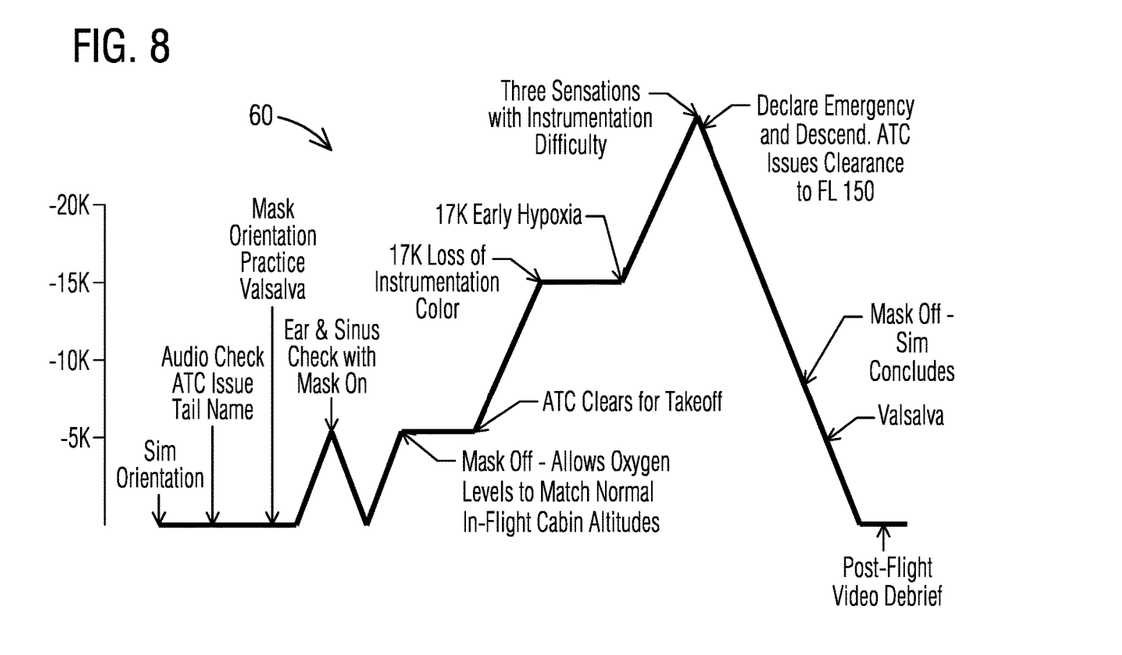
FIG. 8 is a graph that illustrates an example of a simulated altitude of the pressurized chamber over the time period of FIG. 5, according to one embodiment.

FIG. 8 is a graph 60 that illustrates an example of a simulated altitude of the pressurized chamber over the time period of FIG. 5, according to one embodiment. FIG. 8 is a flight table used for this method of training embodying a unique flight profile developed by the inventor whereby the pilots ascend at a rate (e.g. 1500 ft/min) beginning from an initial cabin altitude (e.g. 5000 feet).

In some embodiments, the teaching methodology and apparatus of the present invention are unique as the special headset 12 with original programmed algorithms will alert the pilot 14 via an onboard alarm systems (e.g. buzzer device 46).

In some embodiments, the present invention relates to an original method 100, 150 and training system for pilots who fly pressurized aircraft to teach the dangers of hypoxia in the event of cabin depressurization, which otherwise would result in loss of consciousness or incapacitation. In some embodiments, the present invention is fundamentally unique from existing training programs by the utilization and integration of a wearable biomedical monitoring system (e.g. headset 12) to accurately alert the pilot 14 to a potentially catastrophic event and the use of a new algorithm to detect the onset of a hypoxia event.

In one embodiment the algorithm effectively avoids false alarms by first determining an oxygen saturation level 58 of a pilot (or flight crew member) and if this value has fallen to a predetermined oxygen saturation level threshold, then measures the pilot's heart rate. If the heart rate is increasing and a slope index based on a ratio of a first slope of the oxygen saturation to a second slope of the heart rate is between about −1.00 and −1.25 (i.e. magnitude of slope index is between about 1.0 and about 1.25) then a hypoxia event is indicated and an alarm is activated to warn the pilot to don his oxygen mask.

Although the emphasis of the training according to the present invention has been described in the aviation context, additional training benefits could be applied to commercial suborbital space training as well as firefighters and others who work in dangerous environments where the wearing of suits and masks is required, which thereby requires suit and mask donning training.

In some embodiments, one or more of the findings forming the bases of the present invention (e.g., a constant value for the slope index of the time rate of change of the oxygen saturation and the time rate of change of the heart rate) will hold true for other rates of ascent and descent.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. As used herein, unless otherwise clear from the context, a value is "about" another value if it is within a factor of two (twice or half) of the other value.

What is claimed:

1. A method for determining onset of hypoxia of an aircraft occupant, comprising:
    measuring at least one physiological parameter of the occupant with a first sensor;
    comparing a value of a parameter based on the at least one physiological parameter with at least one threshold value;
    measuring a pressure within a cabin of the aircraft with a second sensor;
    comparing the pressure with a pressure threshold value;
    determining the onset of hypoxia of the occupant based on both of the comparing steps;
    communicating an alert to the occupant using a device detectable by one or more senses of the occupant, said communicating based on the determining step;
    wherein the first sensor is a pulse oximeter, and wherein the at least one physiological parameter is oxygen saturation level and heart rate;
    wherein the measuring of the at least one physiological parameter further comprises;
        measuring the oxygen saturation level over a time period with the pulse oximeter;
        measuring the heart rate over the time period with the pulse oximeter;
        calculating a first slope based on a rate of change of the oxygen saturation level over the time period with a processor;
        calculating a second slope based on a rate of change of the heart rate over the time period with the processor;
        calculating a slope index with the processor based on a ratio of the first slope to the second slope;
        wherein the value of the at least one physiological parameter is a magnitude of the slope index, wherein the at least one threshold value is a range of the slope index indicative of the onset of hypoxia;
        and wherein the comparing the value of the at least one physiological parameter comprises determining whether the magnitude of the slope index is within the range.

2. The method of claim 1, wherein the pulse oximeter is a reflectant pulse oximeter operatively coupled to a headset worn by the occupant.

3. The method of claim 2, wherein the reflectant pulse oximeter is disposed adjacent a base of an earpiece of the headset such that the reflectant pulse oximeter is adjacent an occipital artery of the occupant.

4. The method of claim 1, wherein the communicating the alert further comprises automatically dropping an oxygen mask for the occupant to wear.

5. The method of claim 4, wherein after dropping the oxygen mask, the measuring the at least one physiological parameter comprises;
    measuring the oxygen saturation level over a time period with the pulse oximeter;
    measuring the heart rate over the time period with the pulse oximeter;
    calculating a first slope based on a rate of change of the oxygen saturation level over the time period with the processor;
    calculating a second slope based on a rate of change of the heart rate over the time period with the processor;
    calculating a slope index with the processor based on a ratio of the first slope to the second slope;
    wherein the value of the parameter is a magnitude of the slope index, wherein the at least one threshold value is a range of the slope index indicative of recovery from hypoxia;
    and wherein the comparing the value of the parameter comprises determining whether the magnitude of the slope index is within the range.

6. The method of claim 5, wherein the range is defined between 0.6 and 0.9.

7. The method of claim 1, wherein the value of the parameter is a value of the oxygen saturation level and wherein the at least one threshold value is an oxygen saturation level threshold such that the comparing the value of the parameter comprises determining whether the value of the oxygen saturation level is less than the oxygen saturation level threshold.

8. The method of claim 1, wherein the value of the parameter comprises a value of the oxygen saturation level and a value of the heart rate, wherein the at least one threshold value is an oxygen saturation level threshold and a heart rate threshold such that the comparing the value of the parameter comprises;
    determining whether the value of the oxygen saturation level is less than the oxygen saturation level threshold, and
    determining whether the value of the heart rate is greater than the heart rate threshold.

9. The method of claim 1, wherein the range is defined between 0.9 and 1.4.

10. The method of claim 1, wherein the range is defined between 1.0 and 1.25.

11. The method of claim 1, further comprising determining the at least one threshold value, including:
    positioning one or more human subjects in a chamber;
    adjusting a pressure within the chamber from a first pressure to a second pressure that is less than the first pressure over a time period to simulate an increase in altitude of the aircraft from a first altitude to a second altitude that is greater than the first altitude;
    measuring the oxygen saturation level of the one or more human subjects in the chamber over the time period;
    measuring the heart rate of the one or more human subjects in the chamber over the time period;
    calculating a value of a parameter based on the measured oxygen saturation level and the measured heart rate of the one or more human subjects over the time period; and
    determining the at least one threshold value based on the calculated parameter value.

12. The method of claim 1, wherein the device is a piezoelectric device and wherein the communicating the alert comprises communicating a haptic alert to the occupant using the piezoelectric device operatively coupled to skin of the occupant.

13. The method of claim 1, wherein the device is an audio buzzer device and wherein the communicating the alert comprises communicating an auditory alert to the occupant using the audio buzzer device.

14. The method of claim 1, further comprising communicating a secondary alert to at least one of a control station on the aircraft to alert flight crew of the onset of hypoxia and to a control station of air traffic control to alert air traffic controllers of the onset of hypoxia;

wherein said communicating the secondary alert includes outputting an image on one or more displays at the at least one control station on the aircraft and the control station of air traffic control, wherein the image includes text or symbols to represent the onset of hypoxia of the occupant.

* * * * *